United States Patent [19]
Biegnon et al.

[11] Patent Number: 5,650,425
[45] Date of Patent: Jul. 22, 1997

[54] PERMANENTLY IONIC DERIVATIVES OF STEROID HORMONES AND THEIR ANTAGONISTS

[75] Inventors: Anat Biegnon, Tel Aviv, Israel; Marcus Brewster, Gainesville, Fla.

[73] Assignee: Pharmos Corporation, New York, N.Y.

[21] Appl. No.: 223,074

[22] Filed: Apr. 4, 1994

[51] Int. Cl.$^6$ .......................... A61K 31/14; A61K 31/40; C07C 217/18; C07C 217/20
[52] U.S. Cl. .......................... 514/408; 514/422; 514/643; 514/644; 548/525; 548/578; 564/283; 564/299
[58] Field of Search ................... 564/283, 299; 548/525, 578; 514/408, 422, 643, 644

[56] References Cited

U.S. PATENT DOCUMENTS

| | | | |
|---|---|---|---|
| 2,914,561 | 11/1959 | Allen et al. | 564/324 |
| 2,914,562 | 11/1959 | Allen et al. | 564/324 |
| 2,914,564 | 11/1959 | Allen et al. | 564/324 |
| 2,971,001 | 2/1961 | Palopoli et al. | 546/240 |
| 4,536,516 | 8/1985 | Harper | 514/514 |
| 4,696,949 | 9/1987 | Toivola et al. | 564/299 X |
| 4,973,755 | 11/1990 | Grafe | 564/324 |

FOREIGN PATENT DOCUMENTS

| | | |
|---|---|---|
| 0168175 | 6/1985 | European Pat. Off. . |
| WO92/06068 | 4/1992 | WIPO . |

OTHER PUBLICATIONS

Vr. J. Pharmacol. (1993), 110, 507–517, "A current view of tamoxifen for the treatment and prevention of breast cancer", by V. Craig Jordan.

Cancer Drug Design (1986), 1, 259–268, "Analogues of tamoxifen: the role of the basic side–chain. Applications of a whole–cell oestrogen–receptor bindning assay to N–oxides and quaternary salts", by M. Jarman, et al.

Pharmacology 1992; 45, 329–337, "Effects of Nonsteroidal Antiestrogens in the in vitro Rat Uterus", by Begona Cantabrana et al.

Neuroscience Research 4, 65–99 (1971), "Site of Action and Active Form of Local Anesthetics", Toshio Narashashi, et al.

Annals New York Academy of Sciences, "Novel Pure Antiestrogens, Mode of Action and Therapeutic Prospects", by A.E. Wakeling (1991).

Endocrin Therapies of Cancer, "Cancer Chemotherapy", by Bruce A. Chabner et al. (1990).

Reports 1477, vol. 83, No. 20, Oct. 16, 1991, "Acquired Tamoxifen Resistance: Correlation With Reduced Breast Tumor Levels of Tamoxifen and Isomerization of Trans–4–Hydroxytamoxifen", by C. Kent Osborne et al.

Endocrinology, vol. 123, No. 4, 1747–1753, "Differential Induction of Progestin–Binding Sites in Uterine Cell Types by Estrogen and Antiestrogen", by Bruce E. Ennis et al. (1988).

Eur J Cancer, vol. 29A, No. 4, 589–592, 1993, "Breast Cancer Chemoprevention", by Alberto Costa.

Annals of Medicine 25, 105–111, 1993, "Development of a Preclinical Model for Hormonal Therapy of Human Endometrial Carcinomas",by P.G. Satyaswaroop.

Academic Press Limited, Cancer Treatment Reviews (1993), 19 (Supplement B), 11–19, "Impact of adjuvant chemotherapy in breast cancer on response to tamoxifen at relapse", by Philippa G. de Takats, et al.

Endocrinology, 1986, vol. 119, No. 6, 2261–2669, "Antiestrogen Action in the Medial Basal Hypothalamus and Pituitary of Immature Female Rats: Insights Concerning Relationships among Estrogen, Dopamine, and Prolactin", by Thomas W. Toney et al.

Journal of Endocrinology, 1991, 130, 409–414, "Pharmacological charactization of a novel oestrogen antagonist, ZK 119010, in rats and mice", by Y. Nishino et al.

Endocrinology, 1991, vol. 129, No. 3, 1568–1574, "Dose–Dependent Effects of Tamoxifen on Long Bones in Growing Rats: Influence of Ovarian Status", by Lilly Y. Moon.

*Primary Examiner*—Richard L. Raymond
*Attorney, Agent, or Firm*—Pennie & Edmonds

[57] ABSTRACT

The present disclosure relates to compounds of the general formulae:

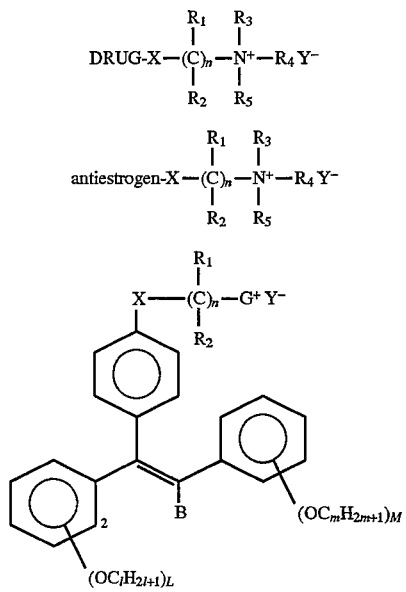

wherein DRUG is a steroid agonist or antagonist, a mixed agonist-antagonist, or a partial agonist, and to the use of such compounds as anti-inflammatory and anti-tumor agents.

39 Claims, 4 Drawing Sheets

PERMANENTLY IONIC DERIVATIVES OF STEROID HORMONES AND THEIR ANTAGONISTS

FIELD OF THE INVENTION

This invention relates to pharmaceutical compositions that are suitable for use in methods of treatment requiring steroid hormones or their antagonists, and to novel permanently ionic chemical compounds that may be used in such methods.

BACKGROUND OF THE INVENTION

In principle, certain types of steroid hormones used in therapeutic procedures might beneficially be excluded from entering the central nervous system (CNS). It would be advantageous to produce derivatives of such hormones that retain their action in peripheral tissues and organs but are devoid of CNS activity. Penetration into the CNS requires that a compound be sufficiently lipophilic to cross the blood brain barrier (BBB). Therefore, to prevent penetration across the BBB it will often suffice to create an ionic drug derivative, especially a derivative that has a large charged moiety attached. However, the receptors through which steroid hormones exert their action are intracellular. Thus, it is not at all obvious that a derivative which is incapable of penetrating the BBB can in fact cross the cell membrane to reach the appropriate receptors. In other words, the cell membrane also constitutes a lipophilic barrier which hinders the passage of charged molecules.

Examples of categories of steroid receptor binding drugs that would beneficially be excluded from the CNS include: corticosteroids, which have been shown to produce neuronal loss; progestins, which are used as an adjunct to estrogen replacement therapy in order to prevent endometrial hyperplasia; and antiestrogens that are used predominantly in preventing or retarding the growth of tumors.

The use of progestins as an adjunct to estrogen in hormone replacement therapy in peri- or postmenopausal women is predicated on their opposition to the effects of estrogen. While estrogen has highly desirable actions in the brain, bone, and cardiovascular system, unopposed estrogen may be undesirable, particularly for the endometrial lining of the uterus. Progestins effectively prevent the undesirable hyperplasia of the endometrium. However, in the CNS they induce depression and hot flushes by virtue of their antiestrogenic activity. The use of progestins limited to their peripheral activity would be advantageous.

Corticosteroids are extremely useful in suppressing inflammatory reactions. Their clinical use is severely curtailed by undesirable side effects, especially during chronic administration (Sapolsky et al. (1985) *J. Neurosci.* 5, 1222–1227; Landfield (1987) *Prog. Brain Res.* 72, 279–300). Many of these adverse side effects could be avoided if these compounds were incapable of exerting their harmful action in the CNS.

Pharmaceutical therapy for breast cancer consists currently of cytotoxic and hormonal agents. Hormonal therapy was developed because, in many women, the breast cancer cells have receptors for the steroid hormone estrogen. The growth of these estrogen receptor-positive cancer cells can be stimulated by estrogen. Antiestrogen therapy attempts to reduce or stop the synthesis of estrogen or to block the action of estrogen on the cancer cell.

Among the hormonals, tamoxifen (U.S. Pat. No. 4,536, 516) holds a preeminent position. Originally designed as an antiestrogen to treat breast cancer in patients with estrogen receptor-positive tumors, the drug was also found to slow the growth of breast cancer in women with estrogen receptor-negative tumors. Tamoxifen is, therefore, useful in most patients. The antiestrogen tamoxifen is particularly effective in delaying recurrence in breast cancer patients and in the palliative treatment of advanced metastatic breast cancer. It is also useful in the treatment of additional types of cancer including prostatic neoplasms (Litherland, S. et al. *Cancer Treatment Reviews,* 1988, 15: 183; Jordan, C., *Br. J. Pharmacol.,* 1993, 110: 507).

Antiestrogens, including tamoxifen, compete with estrogen for receptor sites in cancerous tissues. Occupancy of the receptor site by an antiestrogen fails to elicit the further transcriptional actions generated by estrogens and blocks their activity. It is generally believed that estrogens function by binding to the target cell cytosolic receptors then moving into the cell nucleus and in turn affecting DNA transcription.

Tamoxifen and other antiestrogens also affect cellular, tumor, and organ responses by less direct mechanisms. Antiestrogens penetrate into the CNS and disrupt the normal feedback loops for hormonal balance (hypothalamus-pituitary axis) by blockading estrogen receptors in the anterior pituitary and hypothalamus. Often the physiological activity arising from altered circulating hormone levels is undesirable and leads to a variety of known side effects of antiestrogen administration. Hot flushes, which are CNS-mediated, are the most common side effect of tamoxifen (Jordan, C., ibid.).

The actions of tamoxifen and other nonsteroidal antiestrogens are complicated further by their mixed agonist-antagonist nature. Tamoxifen has partial agonist (estrogenic) activity, and the degree of agonist versus antagonist (antiestrogenic) activity is a function of the target cell (Furr, B. et al., *Pharmacology & Therapeutics,* 1984, 24: 127). Tamoxifen has been shown to act mainly as an antagonist in breast and brain, while its agonistic activity is more apparent in bone and the cardiovascular system.

Whereas it has been postulated that pure antiestrogenic compounds might be more effective antitumor agents, another school of thought asserts that it is advantageous to retain the partial estrogenic activity of these antitumor agents since agonistic estrogenic activity is of proven value in preventing osteoporosis, cardiovascular disorders, and postmenopausal symptoms such as hot flushes (Jordan, C., *Br. J. Pharmacol.,* 1993, 110: 507) and possibly age-related cognitive decline and depression (Sherwin, B., *Psychoneuroendocrinology,* 1988, 13: 345). In particular, it has been envisaged that antiestrogen therapy could be administered prophylactically to healthy women at high risk for developing breast cancer, and large prospective clinical trials are underway to test this concept. It would be very desirable to minimize the deleterious effects of estrogen deprivation (or antagonism) in this population.

Considerable effort has been invested in the development of novel tamoxifen analogs presumed to have improved therapeutic potential, by virtue of increased selectivity as antiestrogenic compounds (e.g. U.S. Pat. No. 4,973,755; EP 0 168,175) or higher affinity for the estrogen receptor (WO 92/06068).

In various cases there have been discrepancies between the activity of tamoxifen derivatives in vitro and in vivo. For example, Foster et al. (*Anticancer Drug Design,* 1986, 1: 245) describes the effect of various tamoxifen hydroxy-derivatives on the growth of MCF-7 breast cancer cell line in culture. Hydroxy tamoxifen derivatives that are highly active in vitro were found to be less active than tamoxifen in vivo against a DMBA-induced estrogen receptor-positive tumor in rats, and only slightly more active against a hormone dependent mammary tumor in mice. However, when 4-hydroxy-tamoxifen itself is administered in vivo, its polarity reduces its ability to cross the cell membrane, thereby reducing its access to estrogen receptors located in the cytoplasm. Indeed, in vivo tests indicate a 4-hydroxytamoxifen to be less active than the native tamoxifen (Foster et al., J. Med. Chem., 1985, 28: 1491).

Jarman et al., Anticancer Drug Design, 1986, 1: 259–268 described the preparation and testing of tamoxifen as well as tamoxifen methiodide, ethyl bromide, and N-oxide. When tested in vitro, these derivatives were reported not to halt the proliferation of breast tumor cell lines grown in culture. The interpretation offered was that the quaternized analogs fail to enter the cells (Jarman, M. et al. ibid.; Canabrana, B., Hidalgo, A. Pharmacology, 1992, 329). It was predicted, therefore, that these compounds would be of no therapeutic value in vivo.

SUMMARY OF THE INVENTION

The present invention provides compounds that act as steroid agonists and/or antagonists in peripheral organs and tissues, as required, while virtually devoid of activity in the central nervous system. Contrary to the teachings of the prior art, it is shown herein that compounds that are rendered ionic can achieve their desired therapeutic action in their target cells, even when they may exert their effects intracellularly.

According to the present invention it is now disclosed that, unexpectedly, ionic derivatives of the antiestrogen tamoxifen which were predicted to be of no value in vivo on the basis of their lack of activity in vitro are in fact more active in vivo than the parent compound.

In view of the robust activity of tamoxifen and other antiestrogens in the brain, apart from the disruption of normal feedback loops for gonadotropic function in the hypothalamic and pituitary regions, it is often desirable to use antiestrogenic agents that do not cross into the CNS and brain. Such peripheral antiestrogens would, in general, exhibit reduced side effects during clinical use and particularly in premenopausal women.

Hydrophilic compounds and particularly compounds with ionic charges (cationic or anionic) are often very poorly distributed into the CNS and brain since a lipophilic barrier (the blood-brain barrier or "BBB") exists. One method for creating a permanent charge on a drug is the incorporation of a quaternary ammonium salt (nitrogen with four carbon atoms attached). Tamoxifen and other antiestrogens that contain an amino group can be quaternized (converted to a quaternary ammonium group) resulting in a permanent positive charge on the parent molecule which should effectively reduce its penetration across physiological membranes that are inherently lipophilic and resistant to penetration of ions, particularly large ions.

In those cases where the drug contains no appropriate amine group, a bridging group can be utilized in order to provide an ionizable amine or other ionic species. In the case of progestins bearing a hydroxyl group, such as 17-hydroxy progesterone or medroxypregesterone, a bridging group can be attached in the form of an ester or phosphate or any other suitable species that can provide a permanent ionic moiety. In the case of corticosteroids, the 21-hydroxyl similarly can serve to attach a bridging group for providing an ionic moiety. Thus, by utilizing a strategy involving bridging groups, steroid hormone agonists can be converted to permanently ionic derivatives according to the general precepts of the instant invention.

It is an object of this invention to provide peripheral antiestrogens for clinical treatment of cancer and other diseases and pathological conditions. These peripheral antiestrogens will possess estrogen antagonist activity, and may possess partial estrogen agonist or mixed activity, but are limited in biodistribution by being excluded from the CNS and brain, thereby exhibiting reduced side effects and being beneficial for clinical use. Thus, a primary objective of the present invention is to provide novel compounds that retain antiestrogenic activity in tumor tissue, while rendering them incapable of penetrating into the brain.

Another object of this invention and beneficial to clinical use is the comparatively elevated circulatory levels of these agents due to the fact that they are not sequestered in fat tissue, thereby allowing for more precise control of dosing.

Yet another aspect of this invention is to provide for the formulation and drug delivery of the aforementioned peripheral antiestrogens.

These and other objects of the present invention are achieved by providing compounds of the general formula:

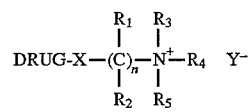

wherein $Y^-$ is any non-toxic pharmaceutically acceptable anion, DRUG is a steroid antagonist, mixed agonist-antagonist, or partial agonist; X is a direct bond or —O—, $NR_6$, —S—, —SO—, —$SO_2$, or —$PO_3$—; $R_1$ and $R_2$ are independently H, alkyl of 1–10 carbon, aralkyl of 7–16 carbons or aryl; $R_3$, $R_4$, $R_5$ are independently branched or unbranched, cyclic or noncyclic alkyl of 1–10 carbons, alkyl of up to 10 carbons atoms substituted by carboxy, hydroxy, alkoxy, halo, or nitro, branched or unbranched, cyclic or noncyclic arylalkyl of 7–16 carbons, aryl; n is 0–12, as well as by providing compounds according to the formula

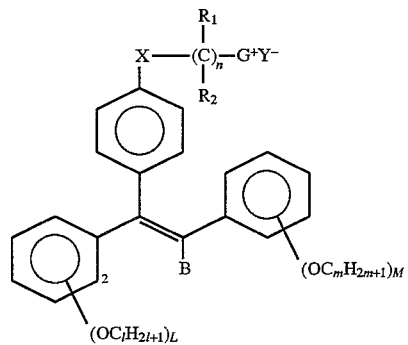

wherein X is a direct bond or is —O—, —$NR_6$—, —S—, —SO—, —$SO_2$—, or —$PO_3$—; $R_1$, $R_2$, and $R_6$ are independently H, alkyl of 1–10 carbons, aralkyl of 7–16 carbons, or aryl; n is 0–12; G is a moiety selected from the group consisting of —N(R') (R") (R'''), —(O)N(R') (R"), —S (R') (R"), and —P(R') (R") (R'''), wherein R' is alkyl of 1–10 carbon atoms, alkyl of up to 10 carbons atoms substituted by carboxy, hydroxy, alkoxy, halo, or nitro, cycloalkyl of 4–8 carbon atoms, cycloalkyl-alkyl of 5–18 carbon atoms, or aralkyl of 7–16 carbons atoms and R" and R''' are independently $C_1$–$C_7$ alkyl and R" and R''' together with N may form a 4- to 8- membered ring; B is $C_pH_{2p+1}$, halo, nitro, or a moiety which is linked to the 2-position of the phenyl that is neither the phenyl linked to the same ethylene carbon as B nor the phenyl substituted by the radical containing the permanently ionic group G, said moiety being selected from the group consisting of —$CH_2C(R_1)(R_2)$— and —$CH_2$—O—; L and M are independently 0–3; l, m, and p are independently 1–7; and Y is a pharmaceutically acceptable anion, provided that when G is —N(R') (R") (R''') or —(O)N(R') (R"), R' and R" cannot both be unsubstituted alkyl.

DETAILED DESCRIPTION OF THE INVENTION

Figure 1:
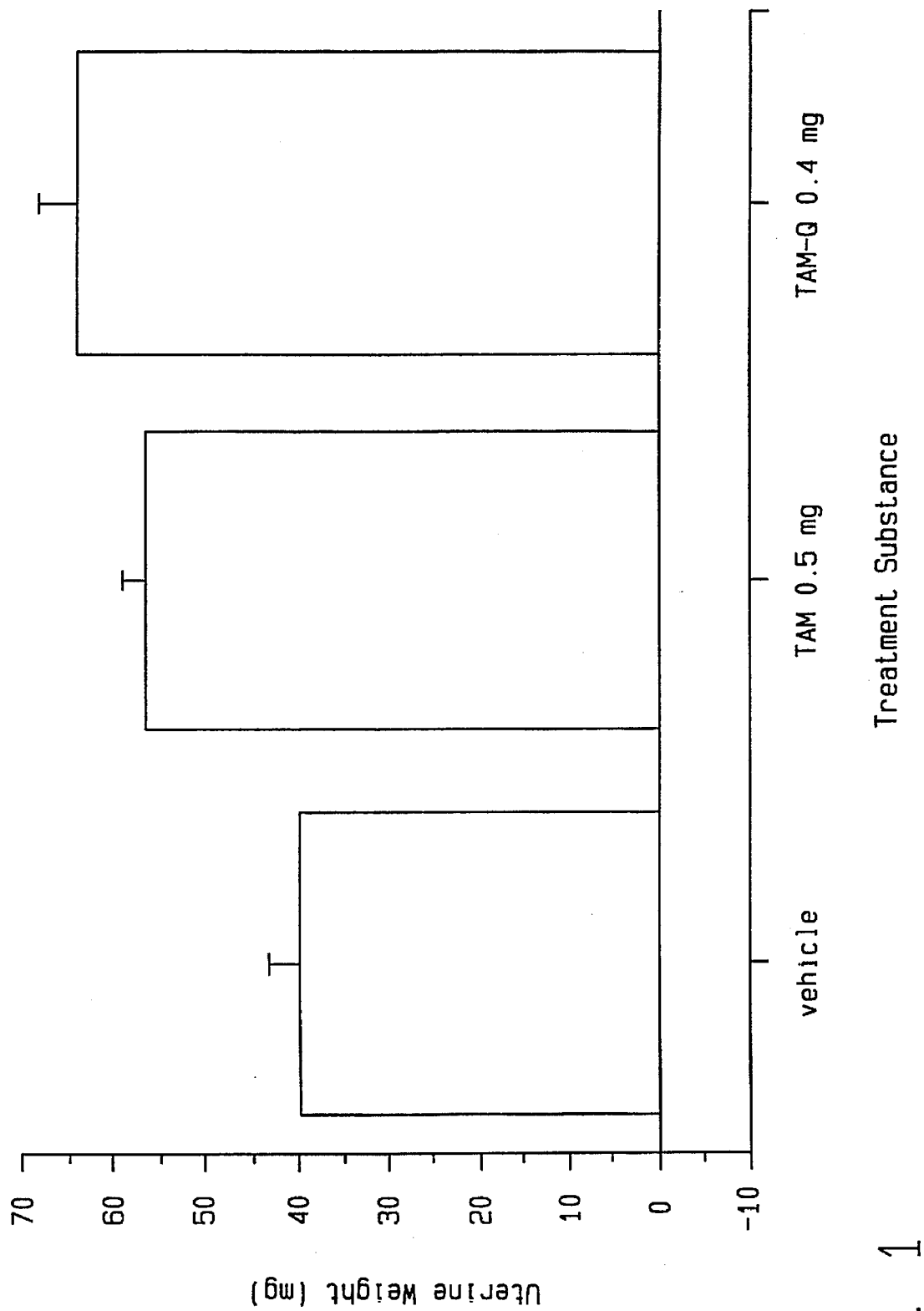
FIG. 1 compares the effects of tamoxifen and of tamoxifen methiodide on uterine weight.

The present invention provides novel pharmaceutical compositions that act as steroid agonists or antagonists or have mixed agonist-antagonist activity with the limitation that these molecules have a permanent ionic moiety that prevents their penetration into the CNS. Contrary to the teachings of the prior art, these permanently charged derivatives of drugs can achieve their desired therapeutic activity in target cells even when the receptors may be located intracellularly.

Accordingly, the present invention provides novel pharmaceutical compositions that retain antiestrogenic activity in tumor tissue while being largely incapable of penetrating into the brain. More specifically compounds according to the present invention provide anti-tumor activity in the breast or other reproductive organs and additionally provide partial estrogenic activity in organs such as bone or the cardiovascular system where estrogen activity is beneficial. A most preferred embodiment of the present invention is devoid of CNS activity, due to its inability to cross the BBB, while simultaneously being efficacious as an anti-tumor agent (irrespective of the mechanisms involved) and as an estrogenic agent in non-tumor tissues.

One aspect of the present invention is pharmaceutical compositions that have anti-tumor activity and that contain as an active ingredient a therapeutically effective quantity of a compound of the formula

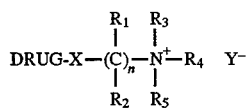

wherein $Y^-$ is any non-toxic pharmaceutically acceptable anion, DRUG is a steroid agonist or antagonist, a mixed agonist-antagonist, or a partial agonist; X is a direct bond or —O—, $NR_6$, —S—, —SO—, —$SO_2$—, or —$PO_3$—; $R_1$ and $R_2$ are independently H, alkyl of 1–10 carbon, aralkyl of 7–16 carbons or aryl; $R_3$, $R_4$, $R_5$ are independently branched or unbranched, cyclic or noncyclic alkyl of 1–10 carbons, alkyl of up to 10 carbons atoms substituted by carboxy, hydroxy, alkoxy, halo, or nitro, branched or unbranched, cyclic or noncyclic arylalkyl of 7–16 carbons, aryl; n is 1–12 or is 0, in which case DRUG or the X moiety is directly attached to the quaternary nitrogen atom.

A preferred subgeneric grouping of said pharmaceutical compositions contains as an active ingredient a therapeutically effective quantity of a compound of the formula

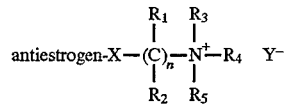

wherein antiestrogen is an estrogen antagonist, mixed agonist-antagonist, or partial agonist and the remaining variables are as defined above.

As discussed in more detail hereinbelow, said pharmaceutical compositions will ordinarily contain a pharmaceutically acceptable diluent or carrier, for instance: a diluent comprising an aqueous cosolvent solution comprising a pharmaceutically acceptable cosolvent, a micellar solution prepared with natural or synthetic ionic or nonionic surfactants, or a combination of such cosolvent and micellar solutions; a diluent consisting essentially of a solution of ethanol, a surfactant, and water; a diluent consisting essentially of an emulsion comprising triglycerides, lecithin, glycerol, an emulsifier, an antioxidant, and water; or a carrier selected from the group consisting of corn starch, lactose, sucrose, sorbitol, talc, stearic acid, magnesium stearate, dicalcium phosphate, and gums.

Said pharmaceutical compositions can be formulated as a tablet for oral dosage, or be otherwise prepared in unit dosage form. A typical daily dosage of said compound will be from about 0.01 to about 10 mg/kg body weight, more preferably, from about 0.05 to about 5 mg/kg body weight.

Also contemplated according to the present invention are methods such as a method of treatment of tumors which comprises administering to a patient a therapeutically effective amount of a pharmaceutical composition as defined above. Thus the present compositions may be used for treating cancer of the breast, ovaries, uterus, or prostate, and for preventing or retarding the growth of cancer, malignant cells, or neoplasms, and for reducing or preventing the metastasis of cancer-cells.

The antiestrogens

Various classes of antiestrogens can be modified in accord with the precepts of the present invention. These include: (a) antiestrogens derived from triphenylethylene, such as tamoxifen, toremifene and clomiphene; (b) antiestrogens derived from diphenyl naphthalene, such as nafoxidine; and (c) antiestrogens derived from triphenyl ethanol, such as ethamoxytriphetol.

Tamoxifen, which has the following formula, may be regarded as a triphenylethylenic antiestrogen.

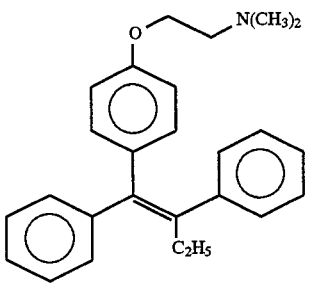

Other triphenylethylenic antiestrogens include enclomiphene,

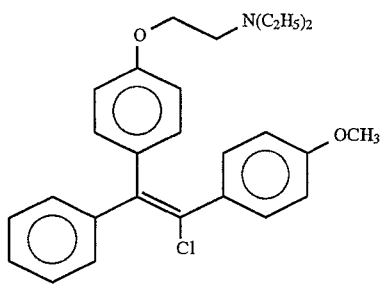

zuclomiphene,

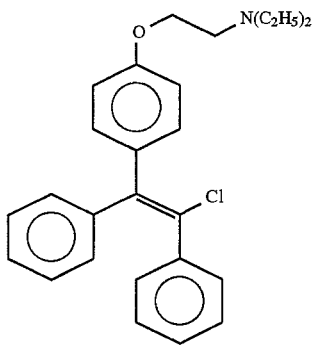

nitromifene,

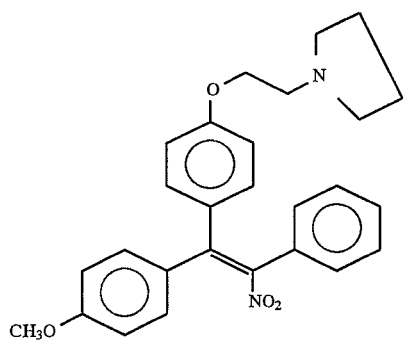

nafoxidene,

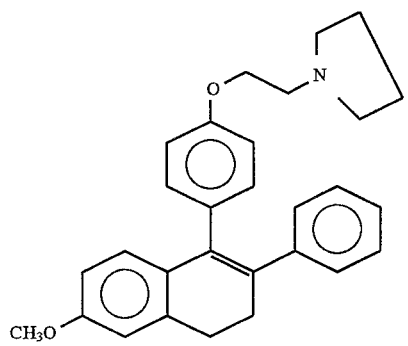

desmethyltamoxifen, toremifene, and desmethyltoremifene.

Structurally similar antiestrogens include ethamoxytriphetol,

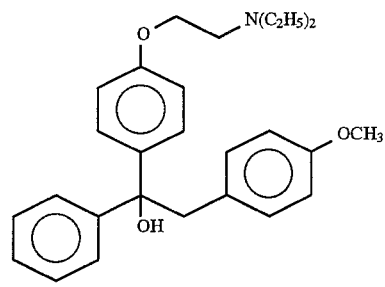

centchroman,

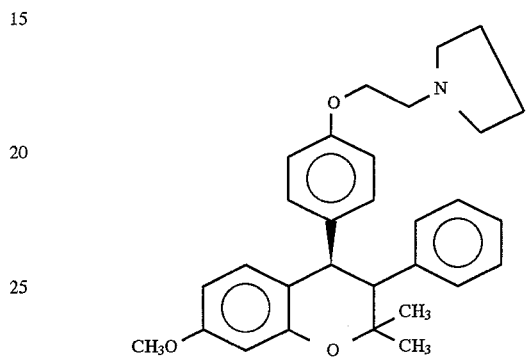

and trioxifene

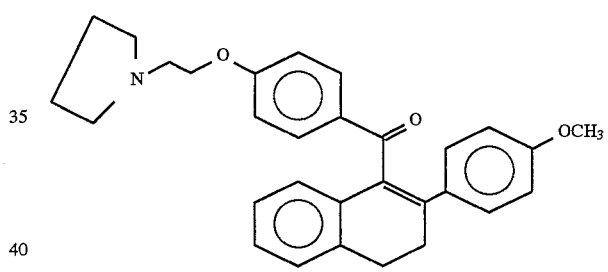

The permanent ionic charge

The modification of drugs to prevent their access to the CNS may be most conveniently accomplished by preparation of quaternary salts. Such compounds may be prepared by a variety of chemical reactions. In the case of antiestrogens containing an amino nitrogen side chain, such as tamoxifen and its analogues, one such method is to react the antiestrogen with an alkylating agent, in order to quaternize the nitrogen atom on the side chain. The alkylating agent can be an alkyl halide, tosylate, alkyl or dialkyl sulfate or any other appropriate moiety. The alkylation may be performed with or without addition of organic solvents, as appropriate, and may be carried out under cooling or at room temperature or with heating, as appropriate, to ensure that the reaction proceeds satisfactorily to completion. However, cooling is preferable whenever cis-trans isomerization is possible. The reaction may be monitored by standard analytical methods known to one skilled in the art including thin layer chromatography, high pressure liquid chromatography, nuclear magnetic resonance spectroscopy or any other suitable method. The resulting quaternary salt is purified by standard methods, known to the artisan, usually including at least one step involving recrystallization. The associated anion may be changed if desired by standard procedures such as ion-exchange columns. Pharmaceutically acceptable anions in accordance with the present invention include citrates, chlorides, bromides, iodides, tosylates, mesylates, sulfates, and in general any anions derivable from alkylating agents or analogues thereof and which are nontoxic.

Pharmacology

The compound provided can be formulated by any required method to provide pharmaceutical compositions suitable for administration to a patient.

The novel compositions contain, in addition to the active ingredient, conventional pharmaceutically acceptable carriers, diluents and the like. Solid compositions for oral administration, such as tablets, pills, capsules or the like, may be prepared by mixing the active ingredient with conventional, pharmaceutically acceptable ingredients such as corn starch, lactose, sucrose, sorbitol, talc, stearic acid, magnesium stearate, dicalcium phosphate and gums, with pharmaceutically acceptable diluents. The tablets or pills can be coated or otherwise compounded with pharmaceutically acceptable materials known in the art to provide a dosage form affording prolonged action or sustained release. Other solid compositions can be prepared as microscapsules for parenteral administration. Liquid forms may be prepared for oral administration or for injection, the term including subcutaneous, intramuscular, intravenous, and other parenteral routes of administration. The liquid compositions include aqueous solutions, with or without organic cosolvents, aqueous or oil suspensions, emulsions with edible oils, as well as similar pharmaceutical vehicles. In addition, the compositions of the present invention may be formed as encapsulated pellets or other depots, for sustained delivery.

The active dose for humans is generally in the range of from 0.01 mg to about 10 mg per kg body weight, in a regimen of 1–4 times a day. However, administration at longer intervals may also be possible, for compounds or formulations having prolonged action. The preferred range of dosage is from 0.05 to 5 mg per kg body weight. It is evident to one skilled in the art that dosage form and regimen would be determined by the attending physician, according to the disease to be treated, method of administration, and the patient's general condition. It will be appreciated that the most appropriate administration of the pharmaceutical compositions of the present invention will depend first and foremost on the clinical indication being treated. The prophylactic treatment of healthy women at high risk for malignant breast tumors will necessitate a sustained maintenance dosage regimen. In contradistinction, the treatment of existing breast cancer will require higher doses at more frequent intervals.

Biological activity

The present invention provides novel medical uses for both known compounds (Jarman et al., Anticancer Drug Design, 1986, 1, 259) and the novel antiestrogen derivatives as described above. These compounds have unexpectedly been shown to possess improved anti-tumor activity when compared to tamoxifen. In addition, these compounds exhibit peripheral estrogenic and antiestrogenic activity in vivo, without appearing to influence the brain. Estrogenic, antiestrogenic, and anti-tumor activity are demonstrated in the Examples hereinbelow.

It should be noted that in those instances where tumor metastases in the CNS may be suspected, the use of non-BBB penetrating compounds of the present invention should not be contraindicated, since tumors in the CNS cause local disruption of the BBB. Indeed, in cases of metastatic brain tumors the use of quaternized anti-tumor agents may achieve preferential drug delivery to the tumor due to the known disruption of the BBB at the tumor site.

EXAMPLES

In order to further illustrate the present invention, specific examples are given below. It is to be understood that the examples given are for illustration only and are in no way limiting.

EXAMPLE 1

Tamoxifen (2.0 g) and methyl iodide (13 ml) were mixed together and the mixture held at 0° C. for 24 hrs. Ethyl acetate (15 ml) was added and the white solid collected by filtration, rinsed with ethyl acetate and dried to afford 2.7 grams of tamoxifen N-methyl iodide (tamoxifen methiodide). All operations were performed at 0°–5° C. to avoid cis-trans isomerization.

EXAMPLE 2

A mixture of tamoxifen (0.5 g) and ethyl iodide (1.5 ml) was stored for 24 hrs at 0°–5° C. Ethyl acetate was added and the solid collected by filtration and rinsed. After drying under vacuum, 0.7 g of tamoxifen N-ethyl iodide were obtained. All operations were conducted at 0°–5° C.

EXAMPLE 3

Analogous to Example 2, tamoxifen (0.5 g), propyl iodide (1.5 ml) and ether (3 ml) were reacted for one week at 0°–5° C. and the resulting white solid was collected by filtration to yield 0.41 g of tamoxifen N-propyl iodide.

EXAMPLE 4

Tamoxifen (0.5 g) and bromomethane (0.25 g) in ether (5 ml) were mixed and held at 0°–5° C. for 24 hours until the initial sticky precipitate converted to a white solid. The white solid was collected by filtration and rinsed with ether. After drying, 0.60 g of tamoxifen N-methyl bromide were obtained.

EXAMPLE 5

Effect of tamoxifen or tamoxifen methiodide on uterine weight in immature female rats: induction and blockade of uterine hypertrophy. Prepubertal female rats respond to treatment by estrogen and estrogen agonists by increase in uterine volume and weight. Antiestrogens are known to block this effect when administered in conjunction with the agonist. Induction of uterine hypertrophy in this model is considered a standard test for in vivo estrogenic activity. Blockade of the estrogen induced response is considered a standard test for antiestrogenic activity in vivo.

Groups of female rats, 22–23 days old, were injected i.p. with 25%/75% ethanol/water (vehicle), tamoxifen (0.5 mg/animal) in 25%/75% ethanol/water suspension, or tamoxifen methiodide (0.4 mg/animal) in 25%/75% ethanol/water suspension. The volume injected was 150 microL. The animals were sacrificed 24 h later and the wet weight of excised uteri determined.

The results of the experiment are presented in FIG. 1. The results were subjected to one-way analysis of variance, and the results are indicated with standard error bars. Tamoxifen ("TAM") and tamoxifen methiodide ("TAM-Q") significantly increased uterine weight. (Overall treatment effect: $P<0.0006$, post-hoc analysis by Scheffe's test: tamoxifen vs. control $p<0.015$, tamoxifen methiodide vs. control $p<0.0008$).

The difference between the native tamoxifen and the methiodide was not significant, but it should be noted that a 20% lower dose of the methiodide was injected, which in tamoxifen equivalents is even lower. This suggests that no biological activity was lost in the tamoxifen derivatization and some may even have been gained.

EXAMPLE 6

In vivo estrogen effects of tamoxifen methiodide on bone: induction of creatine kinase activity in the bone. Estrogens are known to increase the activity of the enzyme creatine kinase (CK) in a number of target organs, including the bone. Compounds increasing bone CK activity are predicted to preserve bone mass, i.e. have estrogen like anti-osteoporosis effects.

Groups of female rats, 22–23 days old, were injected i.p. with 25% ethanol/75% water (vehicle), tamoxifen 0.5 mg/animal in 25% ethanol/75% water suspension, or tamoxifen methiodide 0.4 mg/animal in 25% ethanol/75% water suspension. The volume injected was 150 microL.

Animals were sacrificed 24 h later. Tibia and femur were excised and the epiphyses and diaphyses of the long bones collected and washed thoroughly in cold saline. Tissues were homogenized and centrifuged at 12,000× g for 5 min. The supernatant following this centrifugation was used to assay CK activity (Somjen et al., *Biochem.*, 1991, 277: 863). Enzyme activity was measured on a spectrophotometer at a wavelength of 350 nm. Protein was determined by the Coomasie blue method so that results could be expressed in units as CK specific activity in µmol/min/mg protein.

Figure 2:
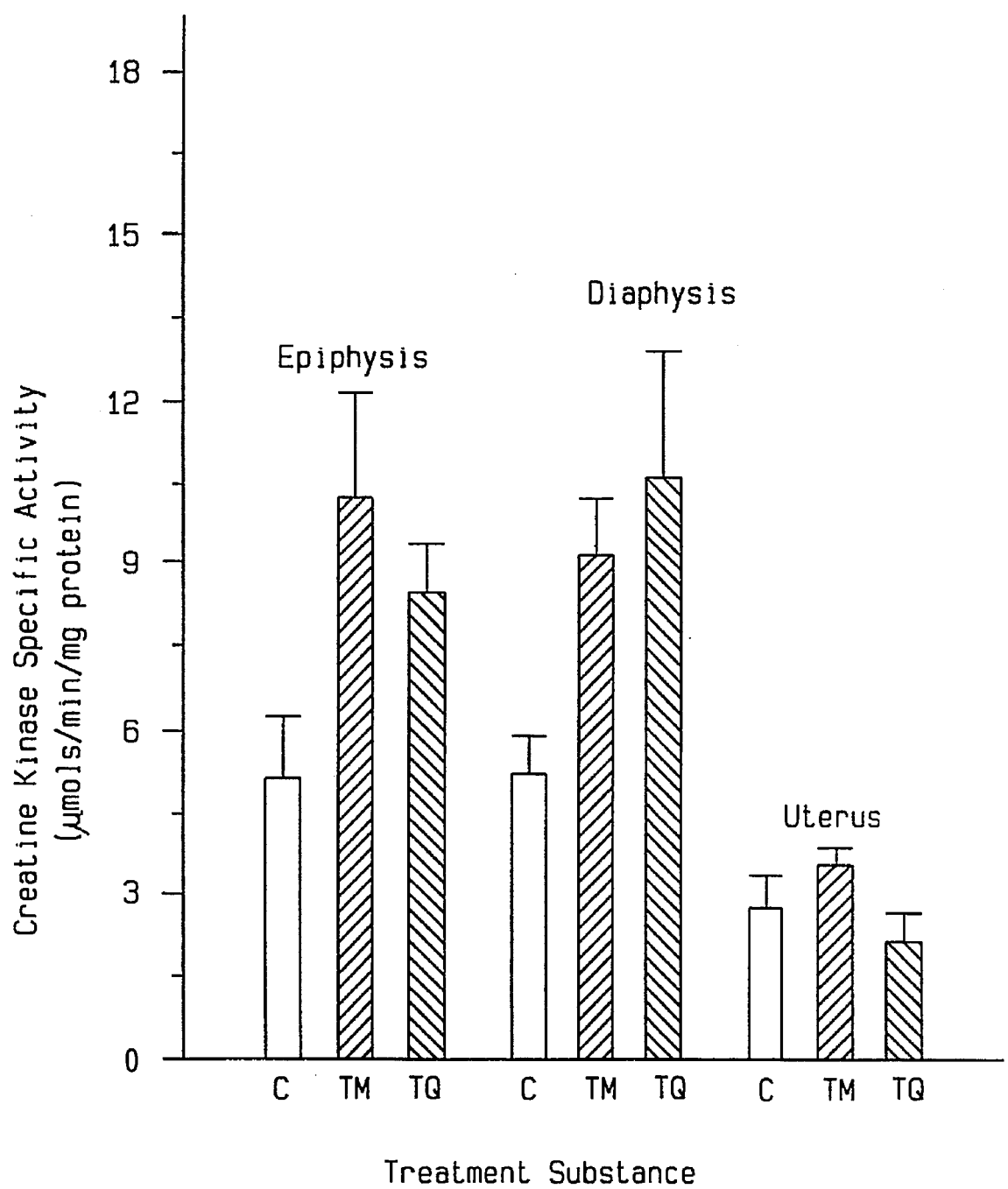
FIG. 2 compares the effects of tamoxifen and of tamoxifen methiodide on creatine kinase activity in bone.

Both treatments nearly doubled CK activity in both tissues (FIG. 2). The increase was highly significant. The effect of tamoxifen methiodide ("TQ") on the diaphysis was actually larger than the effect of tamoxifen ("TM") itself, but this difference did not reach statistical significance.

EXAMPLE 7

Effects of tamoxifen methiodide on body weight changes: induction and blockade of changes in body weight in ovariectomized female rats. Body weight in female rats is tightly regulated by estrogen, which inhibits food and water intake through direct influence on the CNS thereby limiting growth. Ovariectomy results in a cumulative increase in food and water intake and body weight. Estrogen and its agonists prevent this effect of ovariectomy and antiestrogens reverse the outcome of estrogen. Thus, changes in body weight in ovariectomized females are a standard test for estrogenic and antiestrogenic activity. Compounds that do not cross the BBB are not expected to be effective in this model.

Pellets containing either 5 mg tamoxifen or 7 mg tamoxifen methiodide were manufactured by Innovative Research of America (Toledo, Ohio). Pellets containing 100 µg of estradiol-17 β were also supplied by the same manufacturer. This study was designed to continue the evaluation of the antiestrogen effects of TAM and TAM-Q both in the central and peripheral compartments of the rat. Female Sprague-Dawley rats weighing 150–170 g were bilaterally ovariectomized and allowed a 9 day recovery period for the rat to become maximally sensitized to changes in the estrogen environment. Rats were administered either TAM, TAM-Q, estradiol or combinations of the antiestrogen with estrogen (6 animals per composition). All pellets were designed for release of the active compound over 21 days. The experimental groups are presented in Table 1.

TABLE 1

| Animal Group No. | Treatment | | Dose mg Drug/Animal |
|---|---|---|---|
| | Surgery | Therapy | |
| 1 | Ovx | TAM | 15 |
| 2 | Ovx | TAM-Q | 21 |
| 3 | Ovx | TAM/Estradiol | 15/0.2 |
| 4 | Ovx | TAM-Q/Estradiol | 15/0.2 |
| 5 | Ovx | Estradiol | 0.2 |
| 6 | Ovx | Placebo | — |
| 7 | Intact | Placebo | — |

Figure 3:
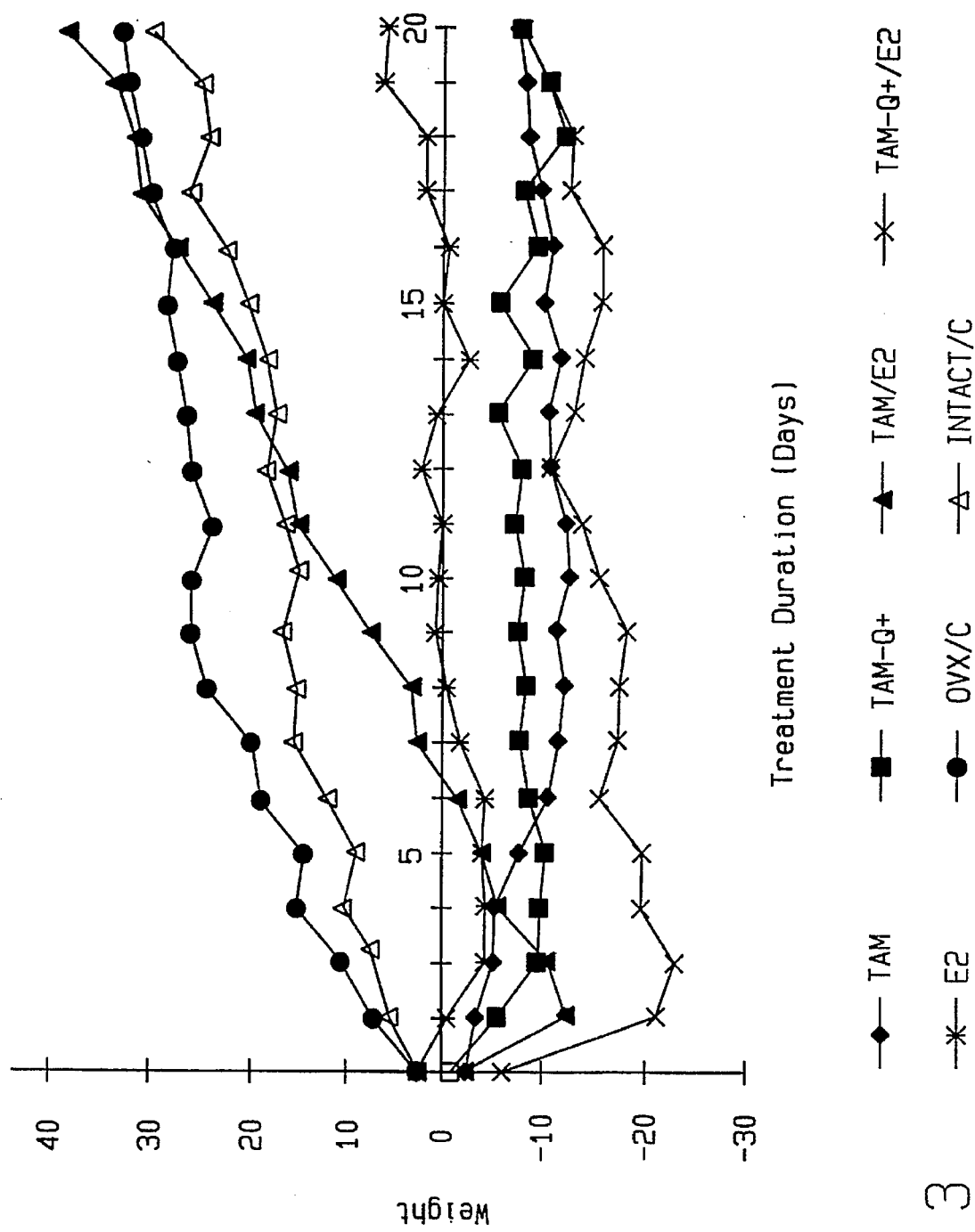
FIG. 3 compares the effects of tamoxifen and of tamoxifen methiodide on body weight.

The in vivo phase of the study is presented in FIG. 3. As can be seen from the results, TAM-Q, unlike TAM, does not block the central effects of estrogen on body weight in these animals, thus indicating that it is not capable of penetrating into the CNS. In contradistinction, as shown in FIG. 1, the quaternized compound (TAM-Q) is efficient in blocking the peripheral effect of estrogen on uterine weight confirming its peripheral antiestrogen effect.

EXAMPLE 8

Brain and plasma levels of tamoxifen methiodide. Adult rats, 4 per group, were injected with tamoxifen methiodide, 0.5 mg/kg or an equimolar dose of tamoxifen (0.36 mg/kg) i.v. in DMSO. Fifteen minutes later, animals were sacrificed and their sera and brains were collected, homogenized and analyzed by HPLC.

The results (Table 2) show fast accumulation of tamoxifen in the brain and very low serum levels at this time point, probably due to sequestration into lipid compartments and elimination. Tamoxifen methiodide, on the other hand, was present in serum at concentrations of 1–2 µg/ml while brain levels were below detection. These results indicate that the quaternization of tamoxifen did, indeed, render it incapable of penetration into the brain.

TABLE 2

| | Serum | Brain |
|---|---|---|
| Tamoxifen | not detectable below 100 nanog/ml | 680 ± 49 nanog/g |
| Tamoxifen methiodide | 1625 ± 110 nanog/ml | not detectable below 100 nanog/ml |

EXAMPLE 9

Anti-tumor activity of tamoxifen methiodide in mice: anti-tumor activity in nude mice implanted with human breast cancer cells. Human breast cancer cells can be grown in culture. Injection of such cells into the flank of genetically athymic nude mice, coupled with estrogen treatment, results in the emergence of a tumor within a few weeks. If left untreated, the tumors will grow over time even after withdrawal of the exogenous estrogen until death of the animals occurs. Tumor size is relatively easy to measure and the ability of compounds to halt, or most preferably to induce regression of tumor growth, is considered a test of their anti-tumor activity.

MCF7 cells (human breast cancer derived cell line) were grown in culture. A total of 30 nude mice were each injected with 2×10$^6$ tumor cells in the flank area. Concomitantly, a subcutaneous estrogen pellet was implanted in the back of the neck. Animals were observed for tumor emergence. When visible tumors were detected (2–4 weeks after implantation), their length, width and height were measured with calipers. The values recorded were multiplied to produce a volume measurement and noted as baseline (time 0) tumor size. At this point, the estrogen pellet was replaced by a blank pellet (9 animals/control group), a tamoxifen methiodide pellet containing a molar equivalent of 5 mg tamoxifen (10 animals), or a tamoxifen 5 mg pellet (9 animals). The pellets were purchased from Innovation Research and were designed to provide 21 days of constant release. Animals were then monitored for tumor growth and general appearance at least once a week over the next six weeks. The changes in tumor size compared to time 0 were calculated as percent change as follows:

$$\frac{(\text{tumor size at time } t - \text{tumor size at time 0})}{(\text{tumor size at time 0})} \times 100$$

Thus, total regression of the tumor will translate into a $-100\%$ change. Statistical analysis of variation with repeated measure revealed highly significant effects of treatment ($p<0.0001$) and time (repeated measure, $p<0.0001$) and a significant interaction ($p<0.0001$). Post-hoc analysis was performed using the Scheffe F test with alpha preset to 0.05.

Figure 4:
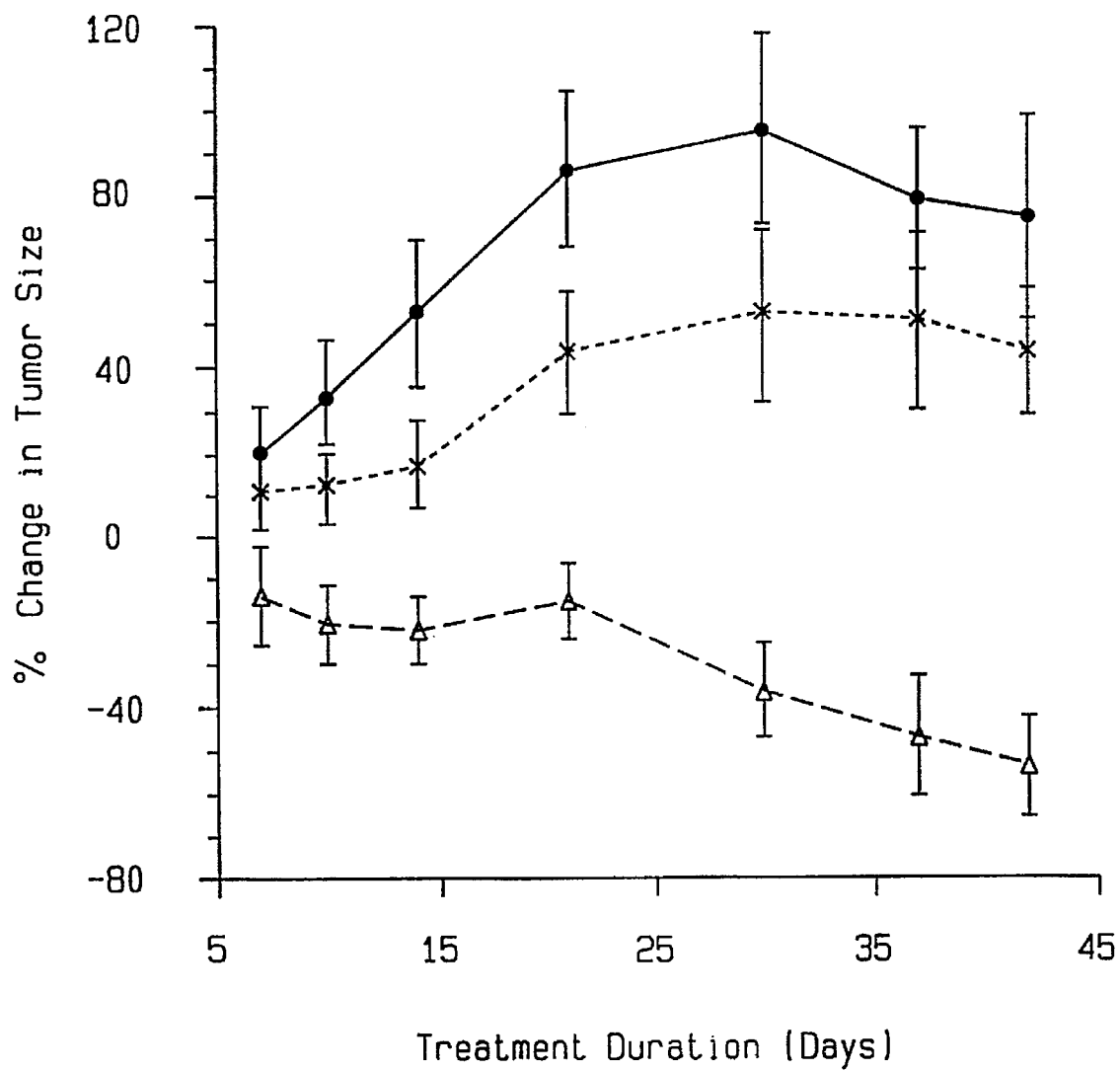
FIG. 4 compares the effects of tamoxifen and of tamoxifen methiodide on breast cancer tumors.

The results of the experiment are summarized in FIG. 4, in which the symbol ● indicates the results obtained with blank pellets, the symbol X indicates the results obtained with tamoxifen pellets, and the symbol Δ indicates the results obtained with tamoxifen methiodide pellets. As can be seen therefrom, tamoxifen methiodide unexpectedly induced significant tumor regression as early as 10 days after implantation of the pellet.

NOVEL COMPOUNDS

As indicated hereinabove, certain of the compounds that can be used in the pharmaceutical compositions and therapeutic methods according to the present invention are known. The following novel compounds, however, constitute in themselves another aspect of the invention herein described.

Permanently ionic compounds having the formulae

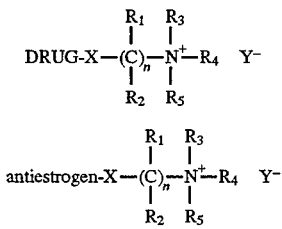

wherein Y− is any non-toxic pharmaceutically acceptable anion, DRUG is a steroid agonist or antagonist, mixed agonist-antagonist, or partial agonist; antiestrogen is an estrogen antagonist, mixed agonist-antagonist, or partial agonist; X is a direct bond or —O—, $NR_6$, —S—, —SO—, —$SO_2$—, or —$PO_3$—; $R_1$ and $R_2$ are independently H, alkyl of 1–10 carbon, aralkyl of 7–16 carbons or aryl; $R_3$, $R_4$, $R_5$ are independently branched or unbranched, cyclic or noncyclic alkyl of 1–10 carbons, alkyl of up to 10 carbons atoms substituted by carboxy, hydroxy, alkoxy, halo, or nitro, branched or unbranched, cyclic or noncyclic arylalkyl of 7–16 carbons, aryl; n is 1–12 or 0, provided that when DRUG or antiestrogen is tamoxifen or 4-hydroxy-2-methyltamoxifen, $R_3$ and $R_4$ are methyl, and $R_5$ is methyl or ethyl, Y is not a halide.

Preferred compounds according to the above formulae are those wherein antiestrogen is selected from the group consisting of tamoxifen, desmethyltamoxifen, toremifene, desmethyltoremifene, clomiphene, nafoxidine, and ethamoxytriphetol.

Another grouping of novel compounds according to the present invention is those compounds having the formula

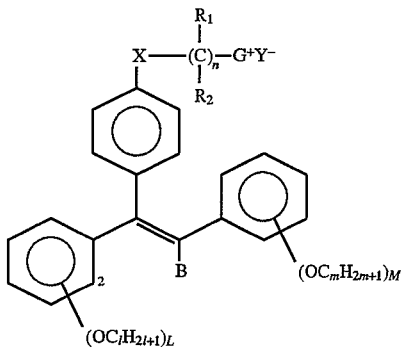

wherein X is a direct bond or is —O—, —$NR_6$—, —S—, —SO—, —$SO_2$—, or —$PO_3$—; $R_1$, $R_2$, and are independently H, alkyl of 1–10 carbons, aralkyl of 7–16 carbons, or aryl; n is 0–12; G is a moiety selected from the group consisting of —N(R') (R") (R'''), —(O)N(R') (R"), —S(R') (R"), and —P(R') (R")(R'''), wherein R' is alkyl of 1–10 carbon atoms, alkyl of up to 10 carbons atoms substituted by carboxy, hydroxy, alkoxy, halo, or nitro, cycloalkyl of 4–8 carbon atoms, cycloalkyl-alkyl of 5–18 carbon atoms, or aralkyl of 7–16 carbons atoms and R" and R''' are independently $C_1$–$C_7$ alkyl and R" and R''' together with N may form a 4- to 8-membered ring; B is $C_pH_{2p+1}$, halo, nitro, or a moiety which is linked to the 2-position of the phenyl that is neither the phenyl linked to the same ethylene carbon as B nor the phenyl substituted by the radical containing the permanently ionic group G, said moiety being selected from the group consisting of —$CH_2C(R_1)$ ($R_2$)— and —$CH_2$—O—; L and M are independently 0–3; l, m, and p are independently 1–7; and Y is a pharmaceutically acceptable anion, provided that when G is —N(R') (R") (R''') or —(O)N(R') (R"), R' and R" cannot both be unsubstituted alkyl.

Preferred compounds of this grouping are those wherein X is —O—; $R_1$ and $R_2$ are H; n is 2; G is —N(R') (R") (R'''); B is $CH_3$, $C_2H_5$, halo, nitro, or a moiety which is linked to the 2-position of the phenyl that is neither the phenyl linked to the same ethylene carbon as B nor the phenyl substituted by the radical containing the permanently ionic group G, said moiety being selected from the group consisting of —$CH_2CH_2$— and —$CH_2$—O—; L and M are 0 or 1, l and m are 1, and p is 2; and Y is a pharmaceutically acceptable anion.

These compounds have utility as peripheral antiestrogens effective in the clinical treatment of cancer and other diseases and pathological conditions. These peripheral antiestrogens will possess estrogen antagonist activity, and may possess partial estrogen agonist or mixed activity. The compounds, however, are limited in biodistribution by being excluded from the CNS and brain, thereby exhibiting reduced side effects. It is this limited biodistribution that significantly enhances the clinical usefulness of the present compounds. Another useful aspect of the compounds of this invention that enhances their attractiveness for clinical use is the comparatively elevated circulatory levels of these agents due to the fact that they are not sequestered in fat tissue, thereby allowing for more precise control of dosing. The use of the present compounds in the treatment of cancerous tumors has been demonstrated above.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims.

What is claimed is:

1. A pharmaceutical composition having bioaffecting activity selected from the group consisting of anti-inflammatory activity and anti-tumor activity which contains as an active ingredient a therapeutically effective quantity of a compound of the formula

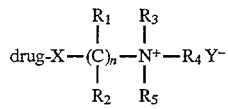

wherein Y— is any non-toxic pharmaceutically acceptable anion, DRUG is a steroid agonist or antagonist, mixed agonist-antagonist, or partial agonist and does not include a triphenyl ethyl or triphenyl ethylene moiety in which the ethyl or ethylene moieties are not additionally substituted; X is a direct bond or —O—, —NR$_6$—, —S—, —SO—, —SO$_2$—, or —PO$_3$—; R$_1$, R$_2$ and R$_6$ are independently H, alkyl of 1–10 carbon, aralkyl of 7–16 carbons or aryl; R$_3$, R$_4$, R$_5$ are independently branched or unbranched, cyclic or noncyclic alkyl of 1–10 carbons, alkyl of up to 10 carbon atoms substituted by carboxy, hydroxy, alkoxy, halo, or nitro, branched or unbranched, cyclic or noncyclic arylalkyl of 7–16 carbons, aryl; n is 0–12; and a pharmaceutically acceptable carrier other than ethanol.

2. A pharmaceutical composition having anti-tumor activity which contains as an active ingredient a therapeutically effective quantity of a compound of the formula

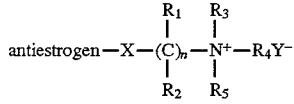

wherein Y— is any non-toxic pharmaceutically acceptable anion, antiestrogen is a steroid agonist or antagonist, mixed agonist-antagonist, or partial agonist and does not include a triphenyl ethyl or triphenyl ethylene moiety in which the ethyl or ethylene moieties are not additionally substituted; X is a direct bond or —O—, —NR$_6$—, —S—, —SO—, —SO$_2$—, or —PO$_3$—; R$_1$, R$_2$ and R$_6$ are independently H, alkyl of 1–10 carbon, aralkyl of 7–16 carbons or aryl; R$_3$, R$_4$, R$_5$ are independently branched or unbranched, cyclic or noncyclic alkyl of 1–10 carbons, alkyl of up to 10 carbon atoms substituted by carboxy, hydroxy, alkoxy, halo, or nitro, branched or unbranched, cyclic or noncyclic arylalkyl of 7–16 carbons, aryl; n is 0–12; and a pharmaceutically acceptable carrier other than ethanol.

3. A pharmaceutical composition according to claim 1 wherein the carrier is elected from the group consisting of corn starch, lactose, sucrose, sorbitol, talc, stearic acid, magnesium stearate, dicalcium phosphate, and gums.

4. A pharmaceutical composition according to claim 3 formulated as a tablet for oral dosage.

5. A pharmaceutical composition according to claim 1 in unit dosage form.

6. A pharmaceutical composition according to claim 1 wherein the daily dosage of said compound from about 0.01 to about 10 mg/kg body weight.

7. A pharmaceutical composition according to claim 6 wherein said daily dosage is from about 0.05 to about 5 mg/kg body weight.

8. A pharmaceutical composition according to claim 2 wherein antiestrogen is tamoxifen.

9. A pharmaceutical composition according to claim 2 wherein antiestrogen is toremifene.

10. A pharmaceutical composition according to claim 2 wherein antiestrogen is clomifene.

11. A pharmaceutical composition according to claim 2 wherein antiestrogen is nafoxidine.

12. A pharmaceutical composition having antitumor activity which contains a carrier and, as an active ingredient, a therapeutically effective quantity of a compound of the formula

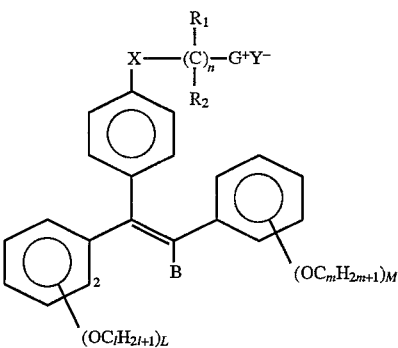

wherein X is a direct bond or is —O—, —NR$_6$—, —S—, —SO—, —SO$_2$—, or —PO$_3$—; R$_1$, R$_2$, and R$_6$ are independently H, alkyl of 1–10 carbons, aralkyl of 7–16 carbons, or aryl; n is 0–12; G is a moiety selected from the group consisting of —N(R') (R'') (R'''), —(O)N(R') (R''), —S (R') (R''), and —P(R') (R'') (R'''), wherein R' is alkyl of 1–10 carbon atoms, alkyl of up to 10 carbons atoms substituted by carboxy, hydroxy, alkoxy, halo, or nitro, cycloalkyl of 4–8 carbon atoms, cycloalkyl-alkyl of 5–18 carbon atoms, or aralkyl of 7–16 carbons atoms and R'' and R''' are independently C$_1$–C$_7$ alkyl and R'' and R''' together with N may form a 4- to 8- membered ring; B is C$_p$H$_{2p+1}$, halo, nitro, or a moiety which is linked to the 2-position of the phenyl that is neither the phenyl linked to the same ethylene carbon as B nor the phenyl substituted by the radical containing the permanently ionic group G, said moiety being selected from the group consisting of —CH$_2$C(R$_1$) (R$_2$)— and —CH$_2$—O—; L and M are independently 0–3; l, m, and p are independently 1–7; and Y is a pharmaceutically acceptable anion.

13. The composition of claim 1 wherein the DRUG comprises a triphenylbutene, toremifene, clomifene, or nafoxidine compound.

14. An ionic compound having the formula

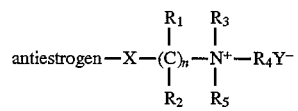

wherein Y is any non-toxic pharmaceutically acceptable anion, antiestrogen is an estrogen antagonist, mixed agonist-antagonist, or partial agonist and does not include a triphenyl ethyl or triphenyl ethylene moiety in which the ethyl or ethylene moieties are not additionally substituted; X is a direct bond or —O—, —NR$_6$—, —S—, —SO—, —SO$_2$—, or —PO$_3$—; R$_1$, R$_2$ and R$_6$ are independently H, alkyl of 1–10 carbon, aralkyl of 7–16 carbons or aryl; $R_3$, $R_4$, $R_5$ are independently branched or unbranched, cyclic or noncyclic alkyl of 1–10 carbons, alkyl of up to 10 carbons atoms substituted by carboxy, hydroxy, alkoxy, halo, or nitro, branched or unbranched, cyclic or noncyclic arylalkyl of 7–16 carbons, aryl; n is 0–12, provided that when antiestrogen is tamoxifen or 4-hydroxy-2-methyltamoxifen, $R_3$ and $R_4$ are methyl, and $R_5$ is methyl or ethyl, Y is not a halide.

15. An ionic compound as in claim 14 having the formula:

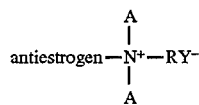

wherein antiestrogen-N-(A)$_2$ is an antiestrogen, estrogen antagonist, estrogen mixed agonist-antagonist, or partial agonist; R is a branched or unbranched, cyclic or non-cyclic alkyl, arylalkyl, or aryl hydrocarbyl group of 1–16 carbons; and $Y^-$ is selected from the group consisting of citrates, chlorides, bromides, iodides, tosylates, mesylates, and sulfates.

16. An permanently ionic compound as in claim 15 wherein antiestrogen is selected from the group consisting of tamoxifen, desmethyltamoxifen, toremifene, desmethyltoremifene, clomiphene, nafoxidine, and ethamoxytriphetol.

17. An permanently ionic compound according to claim 15 wherein antiestrogen is tamoxifen.

18. An permanently ionic compound according to claim 15 wherein antiestrogen is toremifene.

19. An permanently ionic compound according to claim 15 wherein antiestrogen is clomifene.

20. An permanently ionic compound according to claim 15 wherein antiestrogen is nafoxidine.

21. A quaternary salt according to claim 16 wherein R is $CH_3$, X is H and $Y^-$ is a pharmaceutically acceptable anion.

22. An compound of the formula

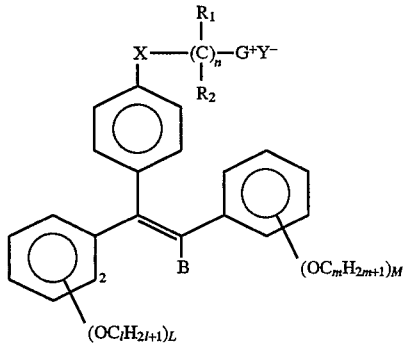

wherein X is a direct bond or is —O—, —NR$_6$, —S—, —SO—, —SO$_2$, or —PO$_3$—; $R_1$, $R_2$, and $R_6$ are independently H, alkyl of 1–10 carbons, aralkyl of 7–16 carbons, or aryl; n is 0–12; G is a moiety selected from the group consisting of —N(R') (R'') (R'''), —(O)N(R') (R''), —S(R') (R''), and —P(R') (R'') (R'''), wherein R' is alkyl of 1–10 carbon atoms, alkyl of up to 10 carbons atoms substituted by carboxy, hydroxy, alkoxy, halo, or nitro, cycloalkyl of 4–8 carbon atoms, cycloalkyl-alkyl of 5–18 carbon atoms, or aralkyl of 7–16 carbons atoms and R'' and R''' are independently $C_1$–$C_7$ alkyl and R'' and R''' together with N may form a 4- to 8- membered ring; B is $C_pH_{2p+1}$, halo, nitro, or a moiety which is linked to the 2-position of the phenyl that is neither the phenyl linked to the same ethylene carbon as B nor the phenyl substituted by the radical containing the permanently ionic group G, said moiety being selected from the group consisting of —C$_2$C(R$_1$) (R$_2$)— and —CH$_2$—O—; L and M are independently 0–3; l, m, and p are independently 1–7; and Y is a pharmaceutically acceptable anion, provided that when G is —N(R') (R'') (R''') or —(O)N(R') (R''), R' and R'' cannot both be unsubstituted alkyl.

23. An compound as in claim 22 wherein X is —O—; $R_1$ and $R_2$ are H; n is 2; G is —N(R') (R'') (R'''); B is $CH_3$, $C_2H_5$, halo, nitro, or a moiety which is linked to the 2-position of the phenyl that is neither the phenyl linked to the same ethylene carbon as B nor the phenyl substituted by the radical containing the permanently ionic group G, said moiety being selected from the group consisting of —CH$_2$CH$_2$— and —CH$_2$—O—; L and M are 0 or 1, l and m are 1, and p is 2; and Y is a pharmaceutically acceptable anion.

24. An ionic compound having the formula

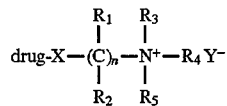

wherein $Y^-$ is any non-toxic pharmaceutically acceptable anion; DRUG is a steroid antagonist, mixed agonist-antagonist, or partial agonist and does not include a triphenyl ethyl or triphenyl ethylene moiety in which the ethyl or ethylene moieties are not additionally substituted; X is a direct bond or —O—, —NR$_6$—, —S—, —SO—, —SO$_2$, or —PO$_3$—; $R_1$, $R_2$ and $R_6$ are independently H, alkyl of 1–10 carbon, aralkyl of 7–16 carbons or aryl; $R_3$, $R_4$, $R_5$ are independently branched or unbranched, cyclic or noncyclic alkyl of 1–10 carbons, alkyl of up to 10 carbons atoms substituted by carboxy, hydroxy, alkoxy, halo, or nitro, branched or unbranched, cyclic or noncyclic arylalkyl of 7–16 carbons, aryl; n is 0–12, provided that when DRUG is tamoxifen or 4-hydroxy-2-methyltamoxifen, $R_3$ and $R_4$ are methyl, and $R_5$ is methyl or ethyl, Y is not a halide.

25. The compound of claim 14 wherein the antiestrogen comprises a triphenylbutene, toremifene, clomifene, or nafoxidine compound.

26. A pharmaceutical composition comprising the ionic compound of claim 14.

27. A pharmaceutical composition according to claim 26 further containing a pharmaceutically acceptable diluent or carrier.

28. A pharmaceutical composition according to claim 27 wherein the diluent comprises an aqueous cosolvent solution of a pharmaceutically acceptable cosolvent, a micellar solution prepared with natural or synthetic ionic or nonionic surfactants, or a combination of such cosolvent and micellar solutions.

29. A pharmaceutical composition according to claim 27 wherein the diluent consists essentially of a solution of ethanol, a surfactant, and water.

30. A pharmaceutical composition according to claim 27 wherein the diluent consists essentially of an emulsion comprising triglycerides, lecithin, glycerol, an emulsifier, an antioxidant, and water.

31. A pharmaceutical composition according to claim 27 wherein the carrier is selected from the group consisting of corn starch, lactose, sucrose, sorbitol, talc, stearic acid, magnesium stearate, dicalcium phosphate, and gums.

32. A pharmaceutical composition according to claim 31 formulated as a tablet for oral dosage.

33. A pharmaceutical composition according to claim 27 in unit dosage form.

34. A pharmaceutical composition according to claim 26 wherein the daily dosage of said compound from about 0.01 to about 10 mg/kg body eight.

35. A method of treatment of tumors which comprises administering to a patient a therapeutically effective amount of a pharmaceutical composition having anti-tumor activity which contains as an active ingredient a therapeutically effective quantity of a compound of the formula

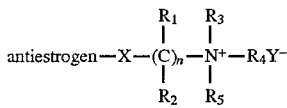

wherein Y— is any non-toxic pharmaceutically acceptable anion, antiestrogen is a steroid agonist or antagonist, mixed agonist-antagonist, or partial agonist; X is a direct bond or —O—, —NR$_6$—, —S—, —SO—, —SO$_2$—, or —PO$_3$—; R$_1$, R$_2$ and R$_6$ are independently H, alkyl of 1–10 carbon, aralkyl of 7–16 carbons or aryl; R$_3$, R$_4$, R$_5$ are independently branched or unbranched, cyclic or noncyclic alkyl of 1–10 carbons, alkyl of up to 10 carbon atoms substituted by carboxy, hydroxy, alkoxy, halo, or nitro, branched or unbranched, cyclic or noncyclic arylalkyl of 7–16 carbons, aryl; and n is 0–12.

36. A method for treating cancer of the breast, ovaries, or prostate which comprises administering a therapeutically acceptable amount of a pharmaceutical composition having anti-tumor activity which contains as an active ingredient a therapeutically effective quantity of a compound of the formula

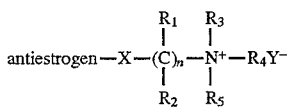

wherein Y— is any non-toxic pharmaceutically acceptable anion, antiestrogen is a steroid agonist or antagonist, mixed agonist-antagonist, or partial agonist; X is a direct bond or —O—, —NR$_6$—, —S—, —SO—, —SO$_2$—, or —PO$_3$—; R$_1$, R$_2$ and R$_6$ are independently H, alkyl of 1–10 carbon, aralkyl of 7–16 carbons or aryl; R$_3$, R$_4$, R$_5$ are independently branched or unbranched, cyclic or noncyclic alkyl of 1–10 carbons, alkyl of up to 10 carbon atoms substituted by carboxy, hydroxy, alkoxy, halo, or nitro, branched or unbranched, cyclic or noncyclic arylalkyl of 7–16 carbons, aryl; and n is 0–12.

37. A method according to claim 36 wherein DRUG is a synthetic antiestrogen.

38. A method for preventing or retarding the growth of cancer, malignant cells, or neoplasms which comprises administering to a subject a therapeutically effective amount of a pharmaceutical composition having anti-tumor activity which contains as an active ingredient a therapeutically effective quantity of a compound of the formula

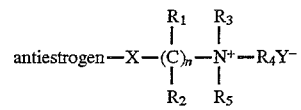

wherein Y— is any non-toxic pharmaceutically acceptable anion, antiestrogen is a steroid agonist or antagonist, mixed agonist-antagonist, or partial agonist; X is a direct bond or —O—, —NR$_6$—, —S—, —SO—, —SO$_2$—, or —PO$_3$—; R$_1$, R$_2$ and R$_6$ are independently H, alkyl of 1–10 carbon, aralkyl of 7–16 carbons or aryl; R$_3$, R$_4$, R$_5$ are independently branched or unbranched, cyclic or noncyclic alkyl of 1–10 carbons, alkyl of up to 10 carbon atoms substituted by carboxy, hydroxy, alkoxy, halo, or nitro, branched or unbranched, cyclic or noncyclic arylalkyl of 7–16 carbons, aryl; and n is 0–12.

39. A method for reducing or preventing the metastasis of cancer-cells which comprises administering a therapeutically effective amount of a pharmaceutical composition having anti-tumor activity which contains as an active ingredient a therapeutically effective quantity of a compound of the formula

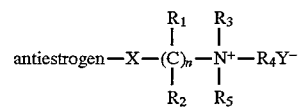

wherein Y— is any non-toxic pharmaceutically acceptable anion, antiestrogen is a steroid agonist or antagonist, mixed agonist-antagonist, or partial agonist; X is a direct bond or —O—, —NR$_6$—, —S—, —SO—, —SO$_2$, or —PO$_3$—; R$_1$, R$_2$ and R$_6$ are independently H, alkyl of 1–10 carbon, aralkyl of 7–16 carbons or aryl; R$_3$, R$_4$, R$_5$ are independently branched or unbranched, cyclic or noncyclic alkyl of 1–10 carbons, alkyl of up to 10 carbon atoms substituted by carboxy, hydroxy, alkoxy, halo, or nitro, branched or unbranched noncyclic or noncyclic arylalkyl of 7–16 carbons, aryl; and n is 0–12.

* * * * *

UNITED STATES PATENT AND TRADEMARK OFFICE
CERTIFICATE OF CORRECTION

PATENT NO. : 5,650,425
DATED : July 22, 1997
INVENTOR(S) : Biegon et al.

It is certified that error appears in the above-indentified patent and that said Letters Patent is hereby corrected as shown below:

On the Title page, item [19] "Biegnon" should read --Biegon--.

Item [75] "Biegnon" should read --Biegon--.

Signed and Sealed this

Twenty-eighth Day of October, 1997

Attest:

BRUCE LEHMAN

Attesting Officer     Commissioner of Patents and Trademarks